United States Patent
Wang et al.

(10) Patent No.: US 9,700,830 B2
(45) Date of Patent: Jul. 11, 2017

(54) PERSONAL CARBON DIOXIDE TRACKER

(71) Applicants: Patrick Wang, Staten Island, NY (US); Benjamin Chin, Rego Park, NY (US)

(72) Inventors: Patrick Wang, Staten Island, NY (US); Benjamin Chin, Rego Park, NY (US)

( * ) Notice: Subject to any disclaimer, the term of this patent is extended or adjusted under 35 U.S.C. 154(b) by 0 days.

(21) Appl. No.: 15/273,944

(22) Filed: Sep. 23, 2016

(65) Prior Publication Data

US 2017/0144100 A1    May 25, 2017

Related U.S. Application Data

(60) Provisional application No. 62/258,436, filed on Nov. 21, 2015.

(51) Int. Cl.

| | | |
|---|---|---|
| *B01D 53/02* | (2006.01) | |
| *B01D 50/00* | (2006.01) | |
| *B01D 24/00* | (2006.01) | |
| *B01D 53/04* | (2006.01) | |
| *G01N 33/00* | (2006.01) | |

(52) U.S. Cl.
CPC ....... *B01D 53/0407* (2013.01); *G01N 33/004* (2013.01); *B01D 2253/102* (2013.01); *B01D 2257/504* (2013.01); *B01D 2259/4143* (2013.01); *B01D 2259/4558* (2013.01)

(58) Field of Classification Search
CPC ............ A61L 9/00; A61L 9/014; B01D 45/00
USPC ............................. 55/315, 522; 96/108; 422/5
See application file for complete search history.

(56) References Cited

U.S. PATENT DOCUMENTS

| | | |
|---|---|---|
| 3,710,553 A | 1/1973 | Parker et al. |
| 3,716,337 A | 2/1973 | Jones |
| 4,297,117 A | 10/1981 | Holter et al. |
| 5,360,002 A | 11/1994 | Smith |
| 6,432,172 B1 | 8/2002 | Lawrence et al. |
| 6,827,760 B2 | 12/2004 | Kutt et al. |
| 6,866,702 B2 | 3/2005 | Mitsuda |
| 7,360,772 B2 | 4/2008 | Koch |
| 7,770,817 B2 | 8/2010 | Macor |
| 8,506,681 B2 | 8/2013 | Paton-Ash et al. |
| 9,089,782 B2 | 7/2015 | Achan, Jr. |
| 9,095,803 B2 | 8/2015 | Augustine et al. |
| 2002/0139251 A1 | 10/2002 | Simmons |
| 2005/0229562 A1* | 10/2005 | Dallas ................ B01D 46/0023 55/486 |
| 2006/0166597 A1 | 7/2006 | Dhillon |
| 2015/0239743 A1 | 8/2015 | Despen et al. |
| 2015/0298043 A1 | 10/2015 | Meirav et al. |

* cited by examiner

*Primary Examiner* — Monzer R Chorbaji
(74) *Attorney, Agent, or Firm* — Collard & Roe, P.C.

(57) ABSTRACT

A device for removing carbon dioxide from the air has a reaction chamber having closed sidewalls and a removable end wall. There is a removable adsorber unit disposed in the reaction chamber that comprises an adsorbent mixture containing soda lime mixed with activated charcoal, and an air-permeable outer covering surrounding the adsorbent mixture. A louvered bed is disposed above the adsorber unit in the reaction chamber. The louvered bed has openings between angled louvers for directing air above the louvered bed into the removable adsorber unit. Air flowing into the reaction chamber is directed toward the adsorber unit by the louvered bed, so that the air flows between the louvers, through the openings and into the adsorber unit where the carbon dioxide in the air is adsorbed and removed from the atmosphere.

9 Claims, 5 Drawing Sheets

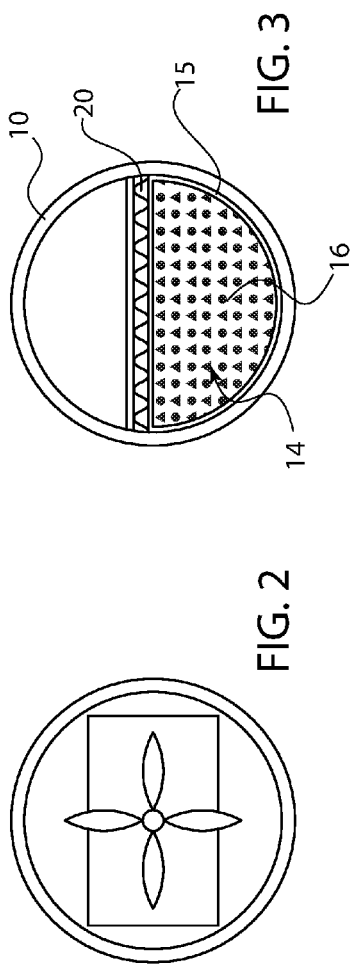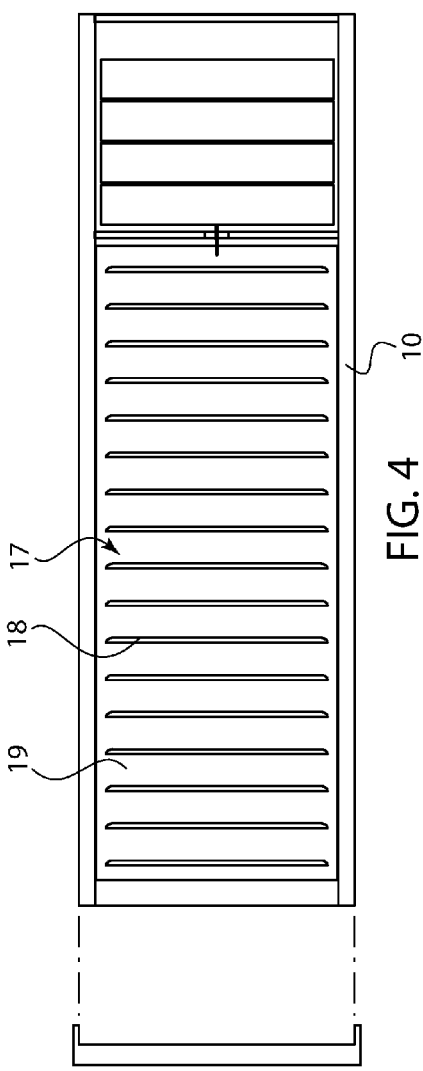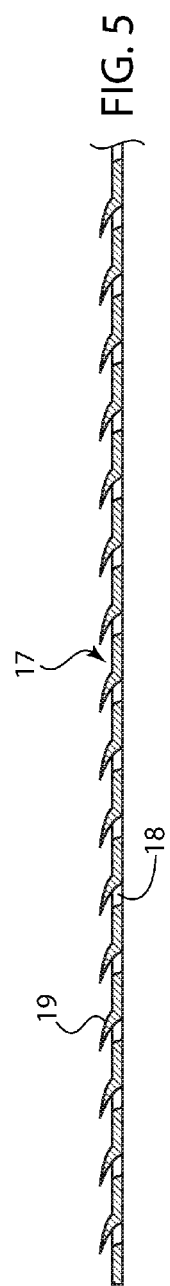

PERSONAL CARBON DIOXIDE TRACKER

CROSS REFERENCE TO RELATED APPLICATIONS

Applicants claim priority under 35 U.S.C. §119(e) of U.S. Provisional Patent Application No. 62/258,436 filed on Nov. 21, 2015, the disclosure of which is incorporated by reference.

BACKGROUND OF THE INVENTION

1. Field of the Invention

This invention relates to a device that adsorbs carbon dioxide from the surroundings and measures the amount that has been removed from the atmosphere. In particular, the invention relates to a portable device that removes $CO_2$ from the air by passing it through a louvered screen and onto a chemical bed that adsorbs the $CO_2$. A sensor and metering device detects the amount of CO2 that is being adsorbed, and tracks this amount over time.

2. The Prior Art

The amount of carbon dioxide in the atmosphere has been increasing over the years, due to increased population and industrial emissions. This increase in $CO_2$ is believed to have caused the current episode of global warming. The global annual mean concentration of $CO_2$ in the atmosphere has increased by more than 40% since the start of the Industrial Revolution, from 280 ppm, the level it had for the last 10,000 years leading up to the mid-18th century, to 399 ppm as of 2015. It would be desirable if individuals could take steps in reducing the $CO_2$ levels in the ambient air, thus reducing the potential for increased global warming.

SUMMARY OF THE INVENTION

It is therefore an object of the present invention to provide a device for removing carbon dioxide from the air that is simple and inexpensive to produce. It is another object of the invention to provide such a device that measures the amount of $CO_2$ that has been removed and which can send the measurements to a central monitoring center. It is yet another object of the invention to provide a device in which the heat generated during $CO_2$ adsorption can be harnessed and used to power the device itself.

These and other objects are accomplished by a device for removing carbon dioxide from the air that has a reaction chamber having closed sidewalls and a removable end wall, the end wall having an opening for allowing air to pass into the reaction chamber and a removable adsorber unit disposed in the reaction chamber. The adsorber unit comprises an adsorbent mixture containing soda lime mixed with activated charcoal, and an air-permeable outer covering surrounding the adsorbent mixture. A louvered bed is disposed above the adsorber unit in the reaction chamber. The louvered bed has openings between angled louvers for directing air above the louvered bed into the removable adsorber unit. This way, air flowing into the reaction chamber is directed toward the adsorber unit by the louvered bed, so that the air flows between the louvers, through the openings and into the adsorber unit.

Once the ambient air reaches the adsorber unit, the carbon dioxide in the air is adsorbed onto the microporous activated carbon, and also reacts with the soda lime. This reaction is exothermic, and heat is released during this process. The reaction is as follows:

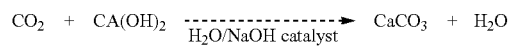

Combining the activated carbon with the soda lime increases the adsorption of $CO_2$, because the activated carbon concentrates the $CO_2$ in the reaction chamber until it is reacted completely with the soda lime. Preferably, the adsorber unit contains soda lime and activated carbon in a 100:1 ratio. Other ratios could also be used.

There is also at least one sensor disposed inside or outside the reaction chamber, the sensor being configured to measure $CO_2$ levels in the chamber. This sensor can be a sensor that senses particle levels of $CO_2$ in the air, such as a non-dispersive infrared sensor, which senses the absorption spectrum of the $CO_2$ molecules by sensing the absorption of infrared radiation by those molecules. The amount of light absorbed at the $CO_2$ wavelength (approx 4.3 µm) is proportional to the gas concentration in the reaction chamber. Alternatively, the sensor could be a temperature sensor that senses the increase in temperature due to the exothermic reaction of the $CO_2$ with the soda lime. This measured heat can then be converted to a measured amount of carbon dioxide that has reacted in the chamber. If the sensor is disposed outside of the reaction chamber, a servo component and tube can be provided to direct air from the reaction chamber to the sensor for measurement purposes.

Connected to the sensor is a processor for collecting data from the sensor and calculating the amount of $CO_2$ in the chamber, as well as the change in $CO_2$ over time. The processor can also be programmed with a baseline $CO_2$ level, either measured by the sensor prior to adsorption or using a known baseline level. The measured $CO_2$ can then be compared to the baseline level over time to determine the amount of $CO_2$ removed from the air. There is also a transmitter connected to the processor for transmitting data from the processor to an outside monitoring center, either directly, or by sending the data to a computer or smartphone which communicates with the monitoring center via the internet. This monitoring center can collect data from several $CO_2$ devices to give data as to the amount of $CO_2$ captured across several units. There can also be a display connected to the processor for displaying the data directly on the device itself. The transmitter can be any suitable wireless transmitter, and can use any suitable means for transmitting the information, such as Wifi, Bluetooth or any other technology. The sensor can be disposed outside the reaction chamber in a separate closed chamber that houses the transmitter and processor, and air can flow through the tube to the sensor in this separate chamber.

The sensor, processor and transmitter are all powered by a power supply such as a battery, which is connected to these units. Alternatively the sensor or other components could be powered by a layer of thermoelectric (TE) fabric disposed beneath the louvered bed. This TE fabric takes the heat generated by the exothermic reaction of the $CO_2$ with the soda lime, and converts it into electrical energy to power the sensor. In one embodiment, the TE generator is made from a carbon nanotube-based polymer composite. Other suitable TE generating materials could also be used.

The TE generator works by converting the temperature differential between the ambient air above the TE generator and the adsorption unit below the TE generator into voltage to power the sensor and/or other components of the device.

The TE generator is connected to the sensor and/or the other components in the device to provide power to these components.

While the device according to the invention is effective without any additional means for drawing air into the reaction chamber, a fan or other device could be used to direct additional air into the reaction chamber. Alternatively, the device could be connected to a moving object such as a bicycle, so that the movement of the bicycle causes air to be drawn into the reaction chamber. The device could also be placed in front of the air conditioning vents in homes or automobiles, so that the air flow is directed into the reaction chamber.

The device could also be equipped with a global positioning system (GPS) module connected to the processor for tracking and recording the location of the device relative to the carbon dioxide adsorption.

Preferably, the reaction chamber, processor, transmitter, GPS and power source are all contained in a common housing, which can be portable. This way, an individual can carry the device around or attach it to their bicycle, car, furniture or any other structure.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 2 is a rear end view;

FIG. 3 is a front end view with the cover removed; and

FIG. 4 is a top view;

FIG. 5 shows a side view of the baffle plate according to the invention;

DETAILED DESCRIPTION OF THE PREFERRED EMBODIMENT

Figure 1:
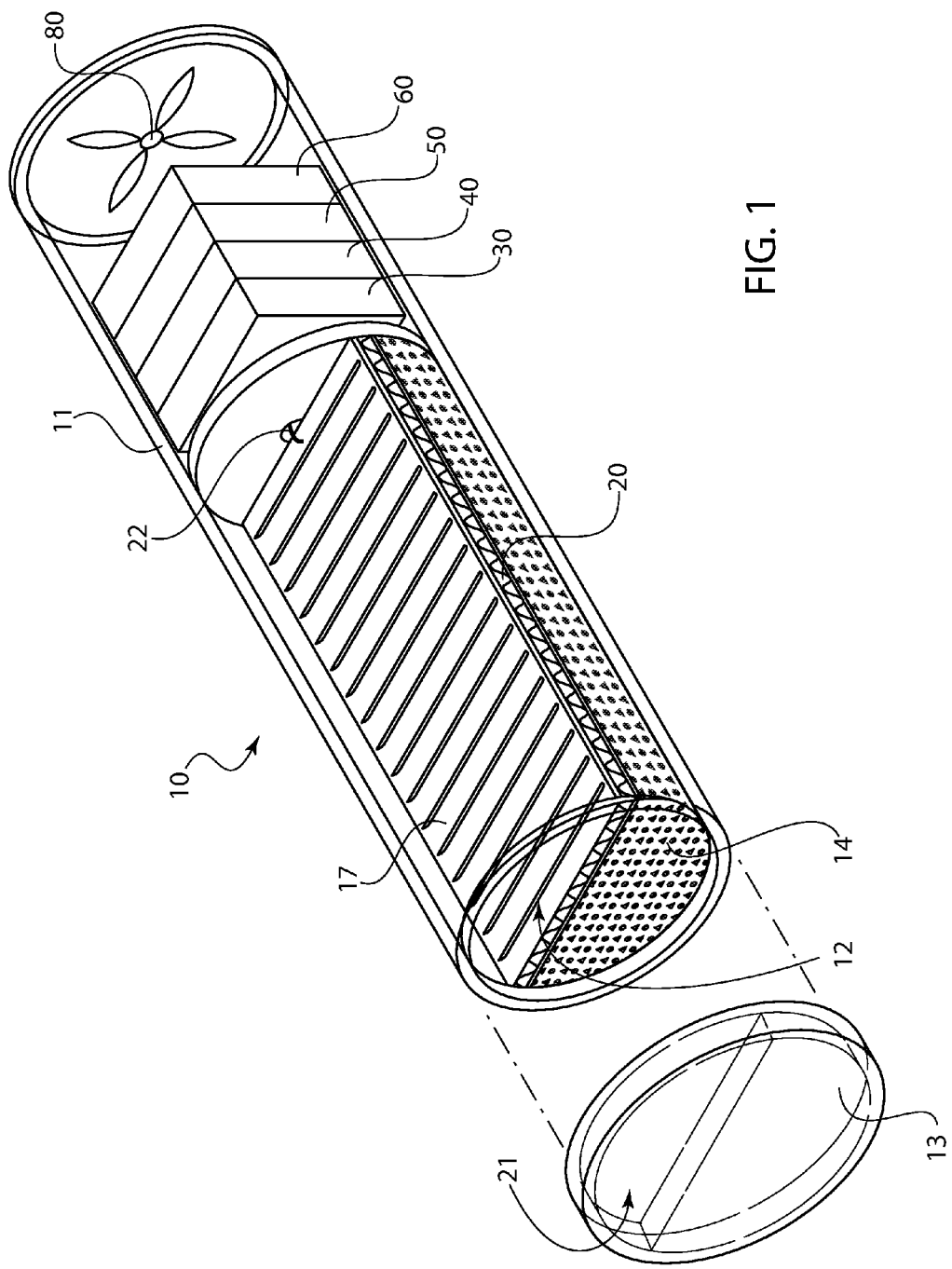
FIG. 1 shows a side view of the device according to the invention.
Figure 6:
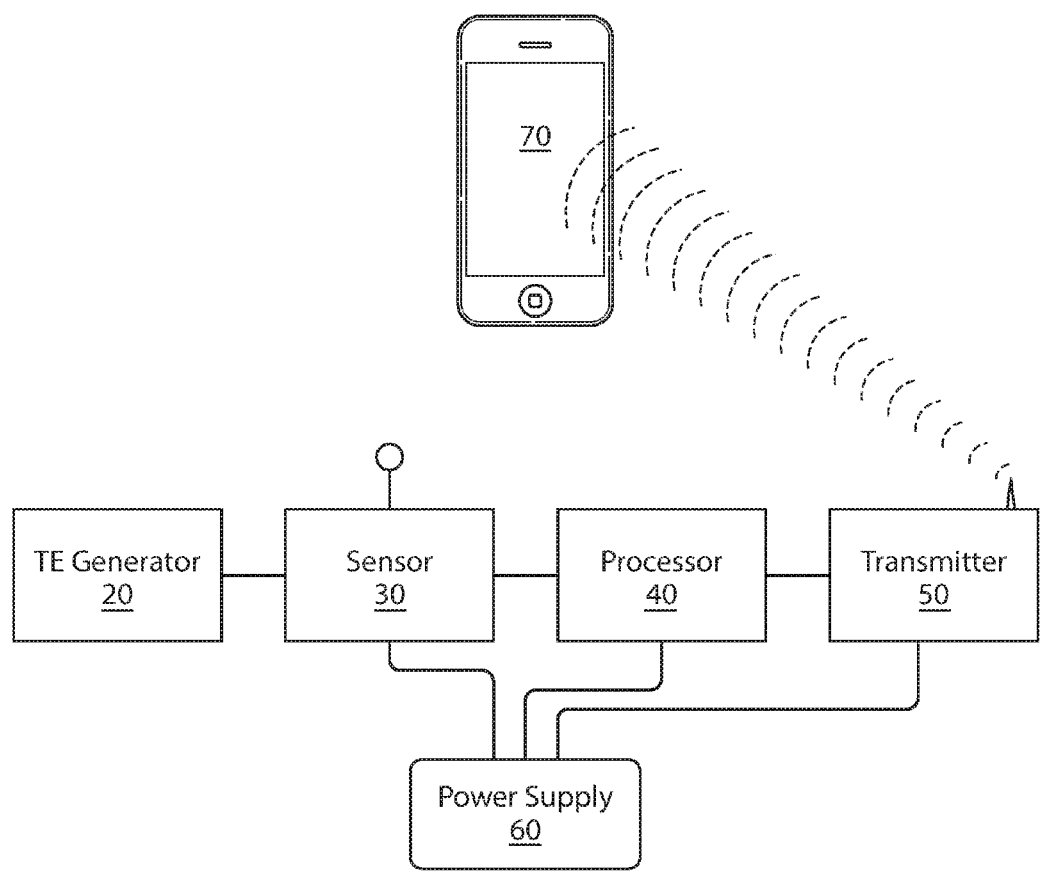
FIG. 6 is a schematic diagram of the various electrical components of the device.

Referring now in detail to the drawings, FIGS. 1-4 show the carbon dioxide tracker 10 according to the invention. Carbon dioxide tracker 10 consists of a housing 11 that houses a reaction chamber 12 in its interior. Housing 11 has an end cap 13 that is open to the air on the top and is closed on the bottom, to keep adsorber unit 14 securely within housing 11. Adsorber unit 14 consists of an outer covering 15 surrounding a mixture of soda lime and activated carbon 16, in a 100:1 ratio. Outer covering 15 is air-permeable so as to allow the $CO_2$ in the ambient air to be adsorbed on the activated carbon and to react with the soda lime in adsorber unit 14. The activated carbon in the adsorber unit 14 also serves to adsorb other harmful chemicals in the air.

Disposed on top of adsorber unit 14 is a baffle plate 17, which contains a series of slits 18 interspersed between raised baffles 19, as shown in FIG. 5. Baffle plate 17 directs air flowing in through opening 21 in cover 13 across baffles 19 and through slits 18 so that the air flow is directed to adsorber unit 14 where the $CO_2$ can be adsorbed and reacted.

On top of adsorber unit 14 is a layer of thermoelectric (TE) fabric 20. TE fabric 20 takes the temperature gradient caused by the exothermic reaction of the soda lime with the $CO_2$ below the fabric vs. the ambient air above the fabric and converts this gradient to voltage. This voltage is used to power components of the system, such as a sensor 30, which senses the amount of $CO_2$ adsorbed by the unit. The exothermic reaction of the soda lime generates energy calculated by $\Delta H° = -5.3$ kJ/mol.

Sensor 30 can be any suitable type of sensor, such as a temperature sensor, which measures the heat generated by the exothermic reaction of the CO2 with the soda lime, or a NDIR infrared gas sensor, or a chemical sensor. Sensor 30 can be disposed either inside reaction chamber 12 or outside reaction chamber 12, but accessible to reaction chamber 12 via an aperture 22 through which the air can flow. The data measured by sensor 30 is sent to a processor 40, which converts the data into quantifiable measurements, and stores these measurements in a database. The data from processor 40 is sent via a transmitter 50 to an outside storage and monitoring center via mobile telephone 70 or other computer. Transmitter 50 can operate via any suitable technology, such as Wifi, Bluetooth®, cellular transmissions or any other suitable technology. The data collected can be used to show daily $CO_2$ adsorption, the total amount of CO2 adsorbed, and the rate of $CO_2$ adsorption, as well as compare the performance of tracker 10 with other trackers. The components of tracker 10 are powered by a power supply 60, such as a battery.

A display (not shown) can be connected to tracker 10 to display the data processed by processor 40.

A fan 80 can also be attached to housing 11 to pull air through the housing to increase the adsorption rate. When the $CO_2$ adsorption rate of the adsorber unit decreases, the adsorber unit needs to be replaced so that fresh chemicals can react with the CO2. The adsorber unit 14 is easily removed by removing cover 13 and a new adsorber unit 14 can be put in its place. The TE fabric can also signal when the soda lime has been exhausted and it is time to change the adsorber unit. When the current generated falls to zero, the processor can signal an alert either audible or visual, via a light or alarm, to indicate that the adsorber unit needs to be replaced.

Figure 7:
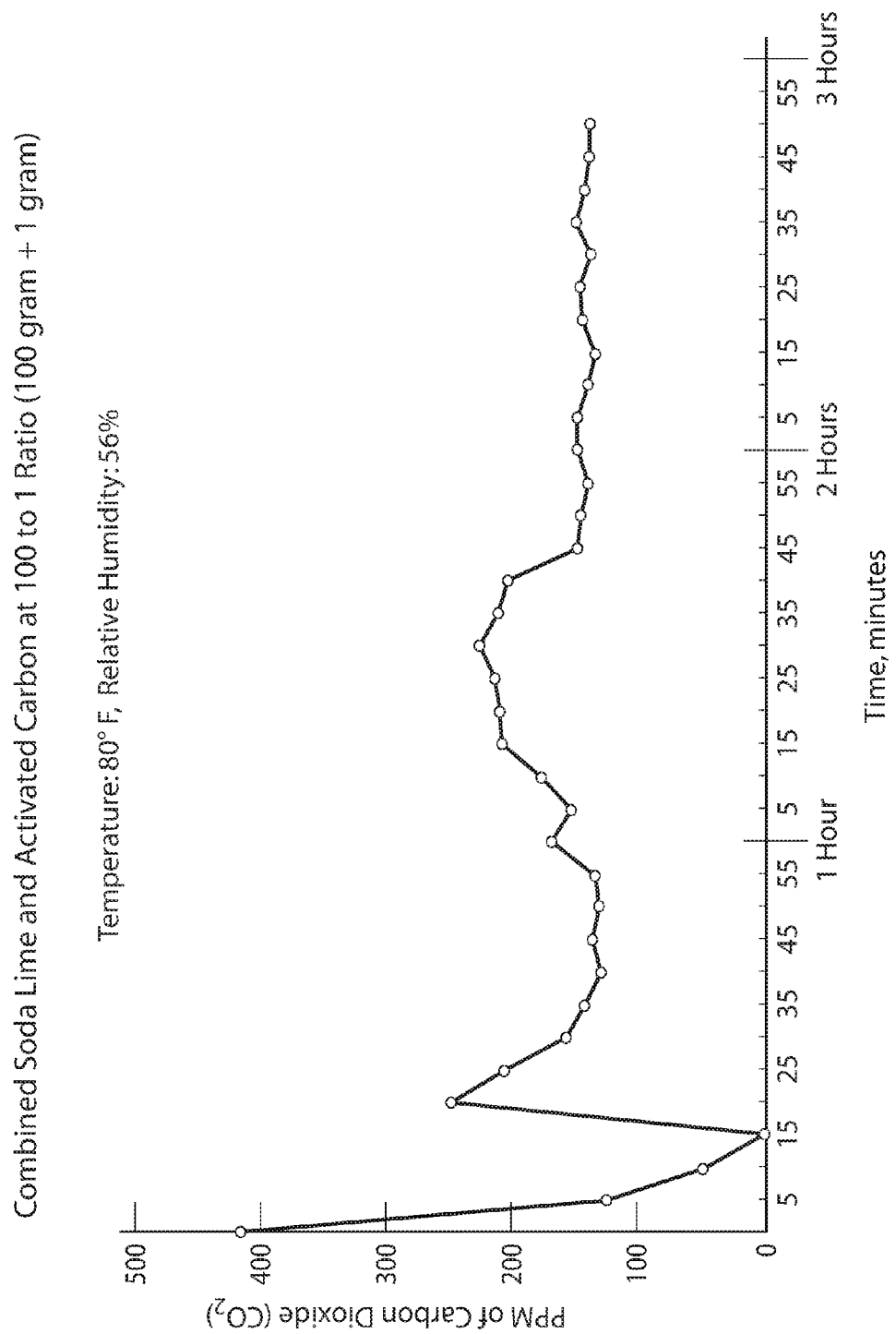
FIG. 7 is a graph showing the CO2 adsorption over time using the activated carbon and soda lime according to the invention.

FIG. 7 is a graph showing the carbon dioxide adsorption in the reaction chamber over time, using a mixture of soda lime and activated carbon in a 100:1 ratio. The $CO_2$ measurements were conducted by a professional Carbon Dioxide Meter Model# CO240 manufactured by EXTECH Instruments. This model also provides temperature and relative humidity. The ambient air had a carbon dioxide content of 403 ppm, an air temperature of 80° F. and a relative humidity of 56%. The $CO_2$ was reduced to zero after 15 minutes of exposure to the mixture. The $CO_2$ gradually increased, but reached a generally steady state amount of about 140 ppm over 2 hours as fresh air is continually fed into the reaction chamber, thus resulting in a large decrease in the $CO_2$ content of the air over time.

Figure 8:
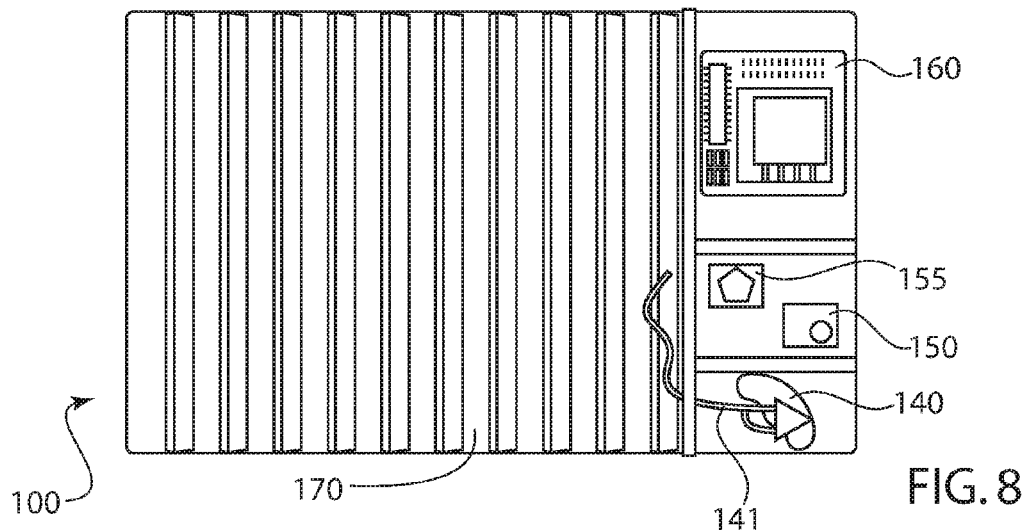
FIG. 8 is top a view of an alternative embodiment of the device according to the invention.
Figure 9:
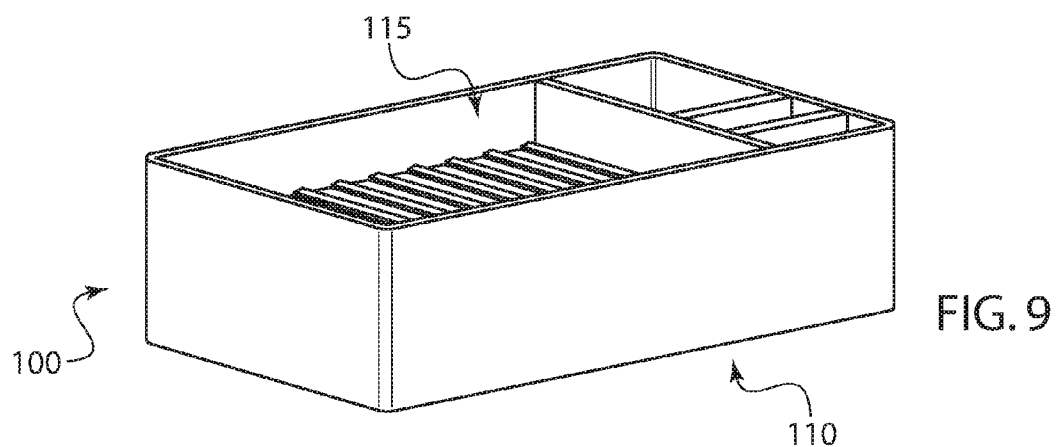
FIG. 9 is a perspective view of the embodiment of FIG. 8.
Figure 10:
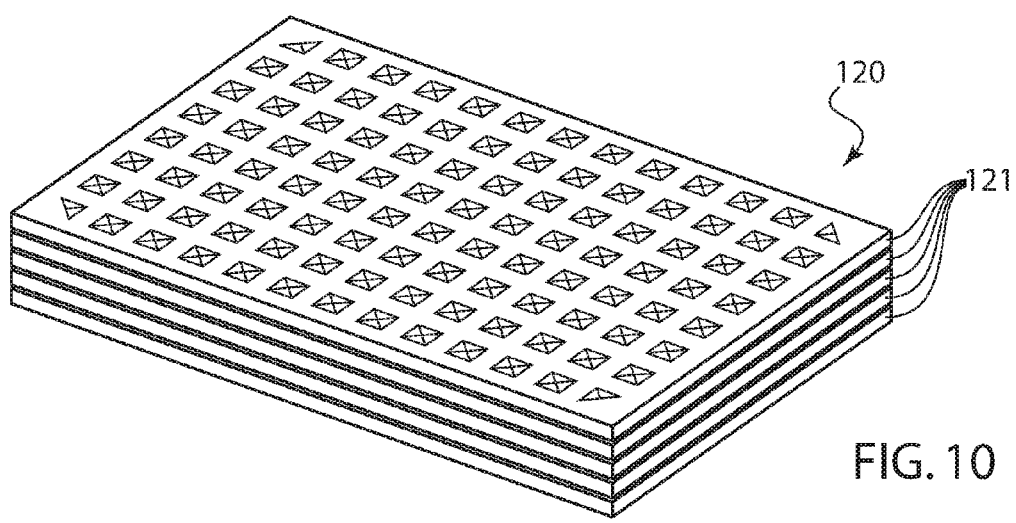
FIG. 10 is a view of an alternative adsorber unit arrangement for use in the embodiment of FIGS. 8 and 9.

FIGS. 8-10 show an alternative embodiment of the CO2 tracker according to the invention. Here, the tracker 100 consists of a rectangular housing 110 in which an adsorber unit 120 is disposed underneath a baffle plate 170, which operates in the same manner as disclosed with respect to FIGS. 1-6. Adsorber unit 120 consists of multiple layers 121, each containing a mixture of soda lime and activated carbon. The layers are adhered together and are inserted and removed from housing 110 as a single unit.

As shown in FIGS. 8 and 9, housing 110 has several compartments, a large one containing the reaction chamber, and several smaller ones, containing the sensors 140, 150, 155, and a processor unit 160 that is a combined processor/transmitter/power source. Sensor 140 is a $CO_2$ sensor that is connected to the reaction chamber 115 by a hose 141, and measures the $CO_2$ inside the reaction chamber 115. Sensors 150, 155 measure the ambient air temperature, humidity and baseline $CO_2$ levels. All of these sensors are connected to processor unit 160.

The embodiment shown in FIGS. 8-10 is particularly suitable for mounting in a car or other larger environment, where the unit is stationary but where air flow from the ventilation system can pass over baffle plate 170 easily. The embodiment shown in FIGS. 1-5 is particularly suitable for mobile applications, such as mounting on a bicycle or scooter, where the unit moves to create air flow.

Accordingly, while only a few embodiments of the present invention have been shown and described, it is obvious that many changes and modifications may be made thereunto without departing from the spirit and scope of the invention.

What is claimed is:

1. A device for removing carbon dioxide from the air, comprising:
    a reaction chamber having closed sidewalls and a removable end wall, the end wall having an opening for allowing air to pass into the reaction chamber;
    a removable adsorber unit disposed in the reaction chamber, the adsorber unit comprising an adsorbent mixture containing soda lime mixed with activated charcoal, and an outer covering surrounding the adsorbent mixture, the outer covering being air-permeable;
    a louvered bed disposed above the adsorber unit in the reaction chamber, the louvered bed having openings between louvers for directing air above the louvered bed into the removable adsorber unit;
    at least one sensor configured to measure $CO_2$ levels in the chamber;
    a processor connected to the sensor for collecting data from the sensor;
    a transmitter connected to the processor for transmitting data from the processor;
    a power source connected to at least one of the sensor, processor and transmitter; and
    a layer of TE generator fabric disposed between the louvered bed and the adsorber unit, wherein the TE generator fabric is configured to convert heat energy emitted by the adsorber unit to electrical energy to power the sensor.

2. The device according to claim 1, further comprising a fan to pull air into the reaction chamber.

3. The device according to claim 1, wherein the adsorber unit contains soda lime and activated carbon in a 100:1 ratio.

4. The device according to claim 1, wherein the power source is a battery.

5. The device according to claim 1, further comprising a display connected to the processor for displaying data measured by the sensor.

6. The device according to claim 1, wherein the sensor is a non-dispersive infrared sensor.

7. The device according to claim 1, wherein the TE generator is made from a carbon nanotube-based polymer composite.

8. The device according to claim 1, wherein the sensor is disposed in the reaction chamber.

9. The device according to claim 1, wherein the sensor is disposed outside of the reaction chamber and wherein air from the reaction chamber is fed to the sensor through a tube.

* * * * *